(12) United States Patent
Dreyer et al.

(10) Patent No.: US 10,107,670 B2
(45) Date of Patent: Oct. 23, 2018

(54) APPARATUS FOR DETERMINING AND/OR MONITORING AT LEAST ONE PROCESS VARIABLE

(71) Applicant: Endress + Hauser GmbH + Co. KG, Maulburg (DE)

(72) Inventors: Volker Dreyer, Lorrach (DE); Sergej Lopatin, Lorrach (DE); Benjamin Mack, Lorrach (DE); Alexander Muller, Sasbach-Jechtingen (DE); Helmut Pfeiffer, Steinen (DE)

(73) Assignee: ENDRESS+HAUSER SE+CO.KG, Maulburg (DE)

( * ) Notice: Subject to any disclaimer, the term of this patent is extended or adjusted under 35 U.S.C. 154(b) by 485 days.

(21) Appl. No.: 14/374,275

(22) PCT Filed: Dec. 17, 2012

(86) PCT No.: PCT/EP2012/075781
§ 371 (c)(1),
(2) Date: Jul. 24, 2014

(87) PCT Pub. No.: WO2013/113446
PCT Pub. Date: Aug. 8, 2013

(65) Prior Publication Data
US 2014/0352427 A1   Dec. 4, 2014

(30) Foreign Application Priority Data
Jan. 30, 2012   (DE) .................. 10 2012 100 728

(51) Int. Cl.
*G01F 23/296*   (2006.01)
*G01N 11/00*   (2006.01)
(Continued)

(52) U.S. Cl.
CPC ........ *G01F 23/296* (2013.01); *G01F 23/2967* (2013.01); *G01N 9/24* (2013.01);
(Continued)

(58) Field of Classification Search
CPC ... G01F 23/296; G01F 23/2967; G01N 11/00; G01N 11/16; G01N 2011/0073; G01N 9/002; G01N 9/24
See application file for complete search history.

(56) References Cited

U.S. PATENT DOCUMENTS 4,922,745 A    5/1990  Rudkin
5,048,323 A    9/1991  Stansfeld
(Continued)

FOREIGN PATENT DOCUMENTS

CN   102177421 A   9/2011
DE     3878473 T3   6/2001
(Continued)

OTHER PUBLICATIONS

German Search Report, German PTO, Munich, dated Nov. 5, 2012.
(Continued)

*Primary Examiner* — Harshad R Patel
*Assistant Examiner* — Punam Roy
(74) *Attorney, Agent, or Firm* — Bacon & Thomas, PLLC (57) ABSTRACT

An apparatus for determining and/or monitoring at least one process variable of a medium in a container comprising an oscillatable unit for introduction into the container; a housing, wherein the oscillatable unit is connected with the housing such that the oscillatable unit closes the housing terminally; at least one hollow space in the oscillatable unit which is accessible from an inner space formed by the housing; and a driving/receiving unit for exciting the oscillatable unit to execute mechanical oscillations and for receiving the mechanical oscillations and for transducing (Continued)

them into an electrical, received signal. Inventive features including that the driving/receiving unit is present in such a manner in the hollow space and that the hollow space is filled with a potting material in such a manner that the driving/receiving unit is connected via the potting material for force coupling with a wall of the hollow space.

13 Claims, 7 Drawing Sheets (51) Int. Cl.
G01N 9/24 (2006.01)
G01N 11/16 (2006.01)
G01N 9/00 (2006.01)

(52) U.S. Cl.
CPC ............. *G01N 11/00* (2013.01); *G01N 9/002* (2013.01); *G01N 11/16* (2013.01); *G01N 2011/0073* (2013.01)

(56) References Cited

U.S. PATENT DOCUMENTS

| | | | |
|---|---|---|---|
| 5,670,709 A | 9/1997 | Gallagher | |
| 5,966,983 A | 10/1999 | Pfeiffer | |
| 6,044,694 A | 4/2000 | Anderson | |
| 6,425,293 B1 | 7/2002 | Woodroffe | |
| 7,530,268 B2 * | 5/2009 | Lopatin | G01F 23/2967 340/621 |
| 8,434,350 B2 | 5/2013 | Lopatin | |
| 2002/0011589 A1 * | 1/2002 | Lopatin | G01F 23/2968 252/500 |
| 2004/0078164 A1 * | 4/2004 | Lopatin | G01F 23/2967 702/100 |
| 2004/0244487 A1 | 12/2004 | Kolosov | |
| 2005/0034521 A1 * | 2/2005 | Lopatin | G01F 23/2967 73/649 |
| 2005/0160806 A1 | 7/2005 | Yoshioka | |
| 2007/0028691 A1 | 2/2007 | Lopatin | |
| 2008/0001501 A1 * | 1/2008 | Lopatin | G01F 23/2966 310/324 |
| 2009/0145656 A1 | 6/2009 | Tschudin | |
| 2010/0154546 A1 * | 6/2010 | D'Angelico | G01F 23/2965 73/632 |
| 2014/0320224 A1 * | 10/2014 | Pfeiffer | G01F 23/2967 331/154 |

FOREIGN PATENT DOCUMENTS

| | | |
|---|---|---|
| DE | 102005013242 A1 | 10/2006 |
| EP | 0023114 A2 | 10/1980 |
| EP | 0070334 A1 | 1/1983 |
| GB | 1581291 | 12/1980 |
| WO | WO 2004094964 A1 * 11/2004 ......... G01F 23/2967 |

OTHER PUBLICATIONS

International Search Report, EPO, The Netherlands, dated Apr. 4, 2013.

English Translastion of the International Preliminary Report on Patentability, WIPO, Geneva, dated Aug. 14, 2014.

* cited by examiner

APPARATUS FOR DETERMINING AND/OR MONITORING AT LEAST ONE PROCESS VARIABLE

TECHNICAL FIELD

The present invention relates to an apparatus for determining and/or monitoring at least one process variable of a medium in a container, comprising an oscillatable unit for introduction into the container, a housing, wherein the oscillatable unit is connected with the housing in such a manner that the oscillatable unit closes the housing terminally, and wherein present in the oscillatable unit is at least one hollow space, which is accessible from an inner space formed by the housing, a driving/receiving unit for exciting the oscillatable unit to execute mechanical oscillations and for receiving the mechanical oscillations and for transducing them into an electrical, received signal, and a control/evaluation unit for controlling the oscillation excitement and for evaluating the received signal with respect to the process variable. The process variable is, for example, the fill level of a bulk good or a liquid and/or the density and/or the viscosity of a liquid or gaseous medium.

BACKGROUND DISCUSSION

Frequently used for fill level measurement, especially for limit level registration, are vibronic measuring devices having an oscillatable unit excitable to execute mechanical oscillations. The oscillatable unit is, in the case of applications in liquids, as a rule, embodied as a so called oscillatory fork having two rods secured on a membrane and acting as the tines of the fork, while for bulk goods both oscillatory forks as well as also single rods having only one resonating rod are applied. Serving for oscillation excitement are, most often, piezoelectric or magnetoelectric drives, which excite the oscillatable unit to its resonant frequency. The piezoelectric drive in the case of oscillatory forks is placed on the rear side of the membrane. The membrane is, in such case, rather thin, in order that a good oscillatory energy transmission takes place between the resonator and the drive. Usually, the membrane is, for instance, 1 to 2 mm thick and its diameter corresponds to 0.5 inch to 1.5 inch. The strength of such membranes is limited in the case of high process pressures and lies typically under 10 MPa.

In the German patent, DE 3878473 T3, a drive technique is described, wherein the oscillatory fork is driven with two piezoelectric elements arranged directly in the tines. An element applied as drive and a piezoelectric element applied as receiving element are respectively mounted on walls of hollow spaces in the tines. In this way, the forces, which the piezo drive delivers, are not transmitted via a membrane, but, instead, directly exerted in root regions of the tines. In this case, the membrane plays a lesser role in the oscillatory system of the sensor and can be as thick as desired. This helps clearly to improve the strength of the sensor under pressure. The application of the piezoelectric drive, and receiving, elements is, in such case, however, relatively difficult to carry out, since the piezoelectric elements must be adhered to the wall and positioned exactly. The exact positioning of the piezoelements plays an important role, since the piezo drive must produce a bending deformation in the transitional region between tines and membrane. Additionally, such a drive is only efficient in the case of metal oscillatory forks.

SUMMARY OF THE INVENTION

An object of the invention is to provide an apparatus of the above-described type, whose drive possesses a high efficiency independently of the material of the oscillatable unit.

The object is achieved by features including that the driving/receiving unit is present in such a manner in the hollow space and the hollow space is filled with a potting material in such a manner that the driving/receiving unit is connected via the potting material for force coupling with a wall of the hollow space. The potting material is especially a hard potting material, so that a force interlocking connection is achieved with very good force coupling between the driving/receiving unit and the oscillatable unit.

In a first embodiment, the driving/receiving unit includes at least one piezoelectric unit in the form of a piezo bimorph. The force interlocking coupling of the piezoelectric unit with the oscillatable unit is produced via the potting material, with which the at least one hollow space is filled.

An embodiment provides that the piezoelectric unit includes a first tablet-shaped piezoelectric element and a second tablet-shaped piezoelectric element, which are connected for force coupling with one another via a respective faces to form a contact surface and which are polarized in the direction perpendicular to the contact surface, wherein at least the respective faces of the piezoelectric elements facing away from the contact surface are provided with electrodes for supplying the exciter signal and for tapping the received signal. The connection between the two piezoelectric elements is preferably produced by means of an adhesive or a solder, so that the two piezoelectric elements are connected with one another via an electrically conductive intermediate layer. In a variant, the piezoelectric elements are polarized in opposed directions and the conductive intermediate layer is connected with the ground potential. In the case of applying an exciter signal in the form of an alternating voltage to the two electrodes, the two piezoelectric elements execute periodic deformations of opposite phase in the form of expansions and shrinkages. In another variant, which likewise leads to a periodic deformation of opposite phase, the intermediate layer is embodied as a third electrode and the three electrodes are supplied with the exciter signal in such a manner that the two outwardly lying electrodes are located at the same potential and the third electrode bears the opposite potential. Bending forces arise in the case of both variants of the piezoelectric unit.

In an alternative embodiment, the driving/receiving unit includes at least one piezoelectric unit having a piezoelectric element and a passive element, wherein the piezoelectric element is contactable with an exciter signal, and wherein the piezoelectric element is connected mechanically with the passive element in such a manner that the supplying of the piezoelectric element with the exciter signal leads to bending deformations of the piezoelectric unit. The passive element is, in such case, composed of a non-piezoelectric material, for example, a ceramic or a metal, and serves to convert the mechanical stresses, which arise from supplying the piezoelectric element with the exciter signal, into a bending deformation. Such a piezoelectric unit is also known under the name, piezo unimorph. In a first variant, the piezoelectric element is provided with electrodes on two oppositely lying faces and is homogeneously polarized. The oppositely lying face, preferably the face in contact with the passive element, lies preferably at the ground potential of the control/evaluation unit. In a second variant, two regions of opposed polarization are provided and the active electrodes are placed on or in the same face, while the oppositely lying face has a shared electrode. Preferably, the shared electrode is located on that face, which is in contact with the passive element. The shared electrode forms preferably a floating ground, i.e. a ground insulated from the ground of the control/evaluation unit.

In an embodiment, at least the oscillatable unit is composed of a synthetic material, e.g. a plastic, or a composite material of synthetic material and glass fibers, glass pearls, carbon fibers and/or ceramic powder. Such composite materials are also referred to as filled synthetic materials and are especially suitable as material for an apparatus of the invention due to their robustness, stability and high mechanical performance. In an especially price favorable variant, also the housing of the apparatus is composed of a synthetic material.

In another embodiment, at least the oscillatable unit is composed of a metal or a metal alloy, a ceramic, a glass or a composite material of ceramic and glass or ceramic and metal.

In an embodiment, at least for the case, in which the oscillatable unit is composed of an electrically conductive material, at least one covering or coating of an electrically insulating material is applied on the driving/receiving unit. In the case of a piezoelectric unit, at least the electrodes are covered with a platelet, e.g. of glass or ceramic, or coated with a coating, preferably of glass or ceramic. Alternatively, the piezoelectric unit can also be potted in an insulating material. For example, the material is a mixture of epoxide resin and corundum powder or glass pearls. This material can also serve as potting material for the hollow space.

An embodiment of the invention provides that the stiffness of the potting material, with which the hollow space is filled, corresponds essentially to the stiffness of the material of the oscillatable unit. In this way, an optimal force transfer from the driving/receiving unit embedded in the potting material to the mechanically oscillatable unit takes place.

In the case of an oscillatable unit formed of synthetic material, the potting material is correspondingly selected in such a manner that its stiffness corresponds to the stiffness of the synthetic material, of which the oscillatable unit is composed. For example, this is the case for an adhesive.

In an embodiment, the potting material, with which the hollow space is filled and/or the material, with which the driving/receiving unit is coated, is composed essentially of epoxide resin, of epoxide resin and corundum powder, epoxide resin and ceramic powder, epoxide resin and sand or of epoxide resin and glass pearls or glass fibers. Suitable for the potting material is especially a composite material of 30 to 60 volume percent epoxide resin and 70 to 30 volume percent corundum powder or glass pearls.

In an embodiment of the apparatus, the oscillatable unit includes a first rod, or paddle, shaped element and a second rod, or paddle, shaped element, which are connected with one another via a base. For accommodating the driving/receiving unit, a first hollow space is provided in a root region of the first element near to the base, and a second hollow space is provided in a root region of the second element near to the base. The rod, or paddle, shaped elements form the tines of an oscillatable unit in the form of an oscillatory fork. The driving/receiving unit includes in the case the oscillatory fork at least two drive units, preferably piezoelectric units, wherein in each of the two rod, or paddle, shaped elements, respectively fork tines, in each case, a drive unit is introducible for exciting the corresponding tine to execute mechanical oscillations.

An advantageous embodiment associated with the embodiment as oscillatory fork provides that at least two piezoelectric units are applied on a board, especially a circuit board, and that the board is embodied in such a manner and the piezoelectric units are arranged on the board in such a manner that the piezoelectric units are introducible into the hollow spaces. The board is a flexible circuit board. The board can, however, also be a rigid circuit board, a plastic board, a film or a sheet.

In an embodiment, the control/evaluation unit supplies the driving/receiving unit with an exciter signal in such a manner that the rod, or paddle, shaped elements execute bending oscillations in opposite directions. In other words, the two rod, or paddle, shaped elements execute oscillations in the fundamental mode.

In a form of embodiment of the apparatus, the oscillatable unit is embodied as a rod-shaped, hollow body with an inner mass formed in an interior of the hollow body on a wall of the hollow body, and the driving/receiving unit is placed in a hollow space provided in the inner mass. In the simplest case, the driving/receiving unit is composed, in such case, of only one piezoelectric unit in the form of a piezo bimorph or piezo unimorph.

In an embodiment, the inner mass is rod-shaped, and the hollow space with the driving/receiving unit is arranged in such a manner that the inner mass and the hollow body execute bending oscillations in opposite directions.

Assembly occurs preferably in such a manner that the hollow spaces of the oscillatory fork, respectively the hollow space of the single rod, are filled with the potting material and the driving/receiving unit is introduced into the still liquid potting material. Then, the potting material cures and the driving/receiving unit becomes affixed in the hollow space. A cumbersome direct applying, especially adhering, of the driving/receiving unit to the wall of the hollow spaces, respectively of the hollow space, is absent. The embodiment of the invention, respectively arrangement of the driving/receiving unit, is especially suitable for measuring devices having an oscillatable unit manufactured of a synthetic material.

BRIEF DESCRIPTION OF THE DRAWINGS

The invention will now be explained in greater detail based on the appended drawing, the figures of which show as follows, in each case, in schematic representation.

DETAILED DISCUSSION IN CONJUNCTION WITH THE DRAWINGS

Figure 1:
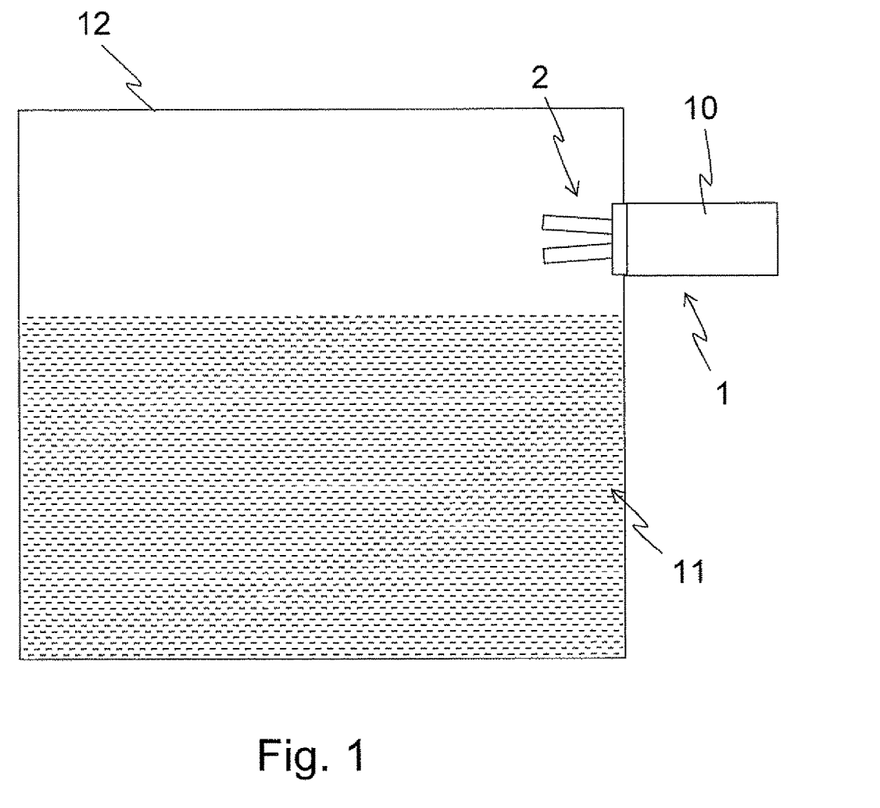
FIG. 1 is a fill-level measuring device in a container.

FIG. 1 shows a container 12 filled with a medium 11, whose limit-level is to be monitored. Mounted at a height in the wall of the container 12 corresponding to the limit-level to be monitored is a measuring device 1 having an oscillatable unit 2. Oscillatable unit 2 possesses two rod-shaped elements 21, 22, which, especially for application in a liquid or a solid, powder-like media, can also be paddle shaped. The two rod-shaped elements 21, 22 protrude into the container 12, while the housing 10 remains outside of the container 12. Arranged in the housing 10 are, for example, electronic components for controlling and/or evaluating the measuring. Oscillatable unit 2 executes mechanical oscillations with the resonant frequency, wherein the two rod-shaped elements 21, 22 execute bending oscillations toward, respectively away from, one another. Detectable from a change of the oscillation frequency is a change of the surrounding medium, in which the oscillatable unit 2 is oscillating, and thereby, the reaching of the limit level to be monitored.

Besides determining or monitoring a fill level of the medium 11, furthermore the density or the viscosity of a liquid is determinable, respectively a limit value for these process variables is monitorable, by means of the measuring device 1 based on the oscillations of the oscillatable unit 2.

In the state of the art, the oscillation excitement is accomplished, as a rule, via a piezoelectric transducer unit, which is arranged on a membrane rear-side, which faces away from the medium 11, and the rod-shaped elements 21, 22 are formed on the other side of the membrane. The transducer unit can be embodied in such a manner that a single piezoelectric element or a piezoelectric element embodied as a bimorph element serves both as transmitter as well as also receiver, or the transducer unit comprises a number of piezoelectric elements, which are respectively transmitters and receivers.

Figure 2:
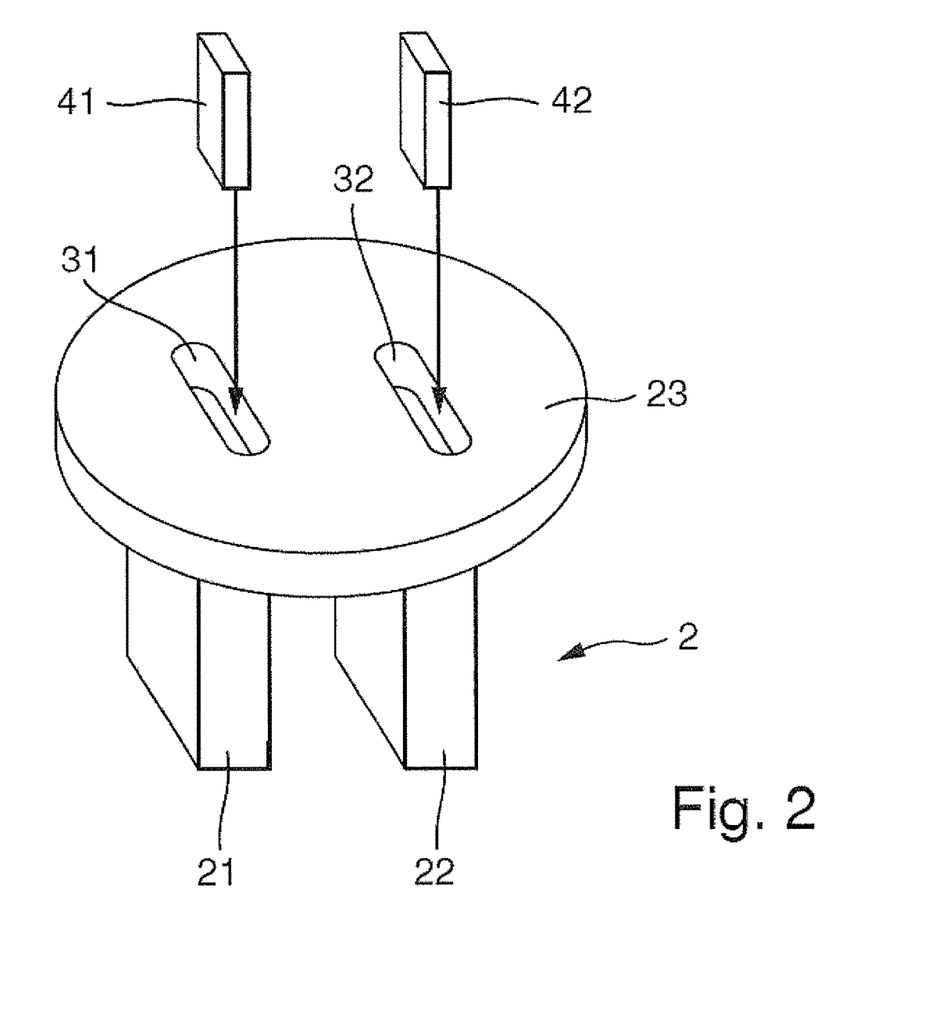
FIG. 2 shows an oscillatable unit in the form of an oscillatory fork having hollow spaces.

According to the invention, the driving/receiving unit is not arranged on a membrane, but, instead, in pocket-like, hollow spaces in the rod-shaped elements 21, 22. This construction is shown in FIG. 2. Various embodiments of the driving/receiving unit 4 are presented in FIGS. 4a-4e.

FIG. 2 shows a schematic view of an oscillatable unit 2 having a first rod-shaped element 21 and a second rod-shaped element 22, which are formed on a circularly shaped base 23. The rod-shaped elements 21, 22 are, in such case, only shown schematically. Preferably, the rod-shaped elements 21, 22 possess a shape matched to the field of application of the measuring device, for example, a paddle shape known from the state of the art for use in liquids or gases.

Base 23 is preferably embodied not thin like a membrane, but is, instead, relatively thick. For example, the thickness of the base 23 amounts to about 3-10 mm in the case of a diameter of 1.5 inch. In an alternative embodiment, base 23 is thin, while the housing adjoining the base 23 is, however, filled, at least in a region near the base 23, with a solid synthetic material. Situated in the base 23 and the rod-shaped elements 21, 22 are two hollow spaces 31, 32. The first hollow space 31 extends into the root region of the first rod-shaped element 21 and the second hollow space 32 extends correspondingly into the root region of the second rod-shaped element 22. Except for the two hollow spaces 31, 32, the rod-shaped elements 21, 22 are solid. Both hollow spaces 31, 32 are accessible from the base 23, so that a first piezoelectric unit 41 is introducible into the first hollow space 31 and a second piezoelectric unit 42 is introducible into the second hollow space 32. The two hollow spaces 31, 32 are dimensioned in such a manner that the piezoelectric units 41, 42 are arranged at least sectionally in the rod-shaped elements 21, 22 and sectionally in the base 23. The piezoelectric units 41, 42 can, however, also be arranged completely in the rod-shaped elements 21, 22.

The two piezoelectric units 41, 42 form the driving/receiving unit 4 of the oscillatory fork and serve, in each case, both for exciting as well as also for receiving mechanical oscillations of the two rod-shaped elements 21, 22. The two flat faces of the piezoelectric units 41, 42 are embodied as electrodes, each of which is contactable via respective connection lines, via which the piezoelectric units 41, 42 can be supplied with an exciter signal and a received signal can be tapped therefrom.

The piezoelectric units 41, 42 are introduced into their respective hollow spaces 31, 32 together with a suitable potting material. The potting material serves to affix the piezoelectric units 41, 42 and to transmit the bending deformations of the piezoelectric units 41, 42 to the rod-shaped elements 21, 22, so that latter execute bending oscillations. The exact position of a piezoelectric unit 41, 42 in a hollow space 31, 32 is insignificant for the oscillation excitement; the piezoelectric units 41, 42 can be oriented parallel, or even maximally inclined, to the side walls of the hollow spaces 31, 32. Since the piezoelectric units 41, 42 need not be exactly positioned and additionally do not need to be secured to walls of the hollow spaces 31, 32, the assembly is especially simple.

The installation of the piezoelectric units 41, 42 is poke-yoke capable, i.e. safe against installation defects. On the one hand, the first piezoelectric unit 41 is identical to the second piezoelectric unit 42, so that the two piezoelectric units 41, 42 are arrangeable exchangeably in the first hollow space 31 or the second hollow space 32. On the other hand, a symmetric embodiment of the piezoelectric units 41, 42 is possible, so that a rotation of 180° in the introduction into the hollow space 31, 32 plays no role. A symmetric embodiment is presented by way of example in FIG. 4a.

The potting material, by means of which the piezoelectric units 41, 42 are potted in the hollow spaces 31, 32, is an adhesive, for example. The potting material is selected in such a manner that the mechanical stresses emanating from the piezoelectric units 41, 42 are effectively transmitted to the rod-shaped elements 21, 22. The stiffness of the potting material for this should correspond about to the stiffness of the material of the oscillatable unit 2. In one embodiment, oscillatable unit 2 is composed of synthetic material, especially a hard synthetic material. Suitable as material for the oscillatable unit 2 is, especially, composite materials, for example, filled or reinforced, synthetic materials, which are reinforced with glass fibers, glass pearls, ceramic powder or carbon fibers. An oscillatable unit 2 of a synthetic material or a composite material is especially simple and cost effectively manufacturable as an injection molded part. A material, whose stiffness corresponds about to that of a synthetic material and, thus, is suitable as filler in the case of a plastic embodiment of the apparatus, or at least of the oscillatable unit 2, is an epoxide resin, especially an epoxide resin having a glass transformation temperature of over 100° C.

In another embodiment, the oscillatable unit 2 is a ceramic part, which is manufacturable, for example, by means of CIM technology, where CIM stands for Ceramic Injection Molding. Suitable ceramics include, for example, aluminum oxide, soapstone, zirconium oxide, porcelain, and silicon carbide. In, again, other embodiments, the oscillatable unit 2 is composed of a glass, for example, borosilicate glass or quartz glass, of a glass ceramic or of a composite of ceramic and glass particles or a composite of ceramic and metal particles.

The illustrated drive is, however, also applicable in the case of usual metal oscillatable units 2. In this case, the piezoelectric units 41, 42 are provided with an insulation, in order to prevent short circuiting with the conductive walls of the hollow spaces 31, 32. The potting material is, in the case of a metal oscillatable unit 2, preferably a solidified adhesive, which contains additives for reinforcement, for example, in the form of particles of corundum, silicon carbide or metal. Advantageous, furthermore, is a small separation between the wall of a hollow space 31, 32 and the piezoelectric unit 41, 42 provided therein.

The introduction of the driving/receiving unit 4 in the form of two piezoelectric units 41, 42 into hollow spaces 31, 32 in the rod-shaped elements 21, 22 with securement by means of potting material leads to a very stable measuring device. Stability in the case of high pressure loading is especially important for oscillatory forks of synthetic material, which are clearly more elastic than metals. A pressure loading can lead not only to a breaking of the synthetic material, but, also, because of an elastic and plastic deformation in the synthetic material, the sensitive piezoceramic components can fracture. If the piezoelectric driving/receiving unit 4 would, such as frequently the case for metal oscillatory forks, be arranged on a base embodied as a membrane, the membrane would be embodied to be relatively thick. This would, however, in the case of the piezoelectric drive secured on the membrane, lead to significant efficiency losses, which can reach such sizes that that the sensor becomes unusable. The construction illustrated in FIG. 2 assures an efficient drive independently of the material of the oscillatable unit 2.

Figure 3:
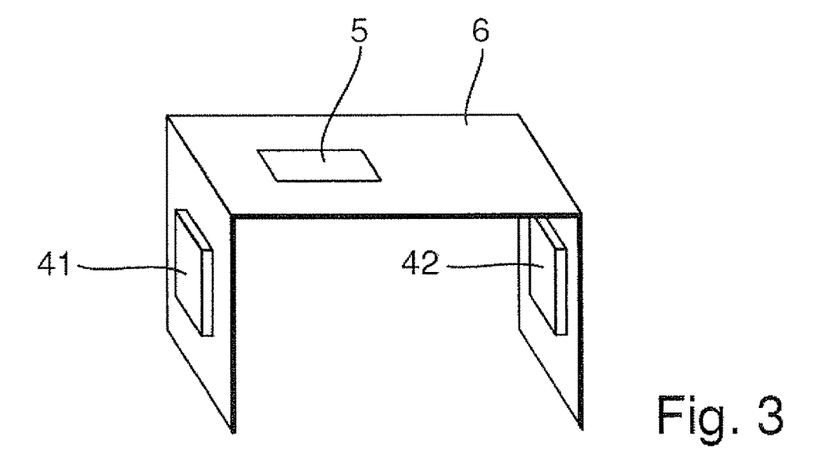
FIG. 3 shows an electronics module with integrated driving/receiving unit.

FIG. 3 illustrates an electronics module, which further simplifies the assembly of the measuring device 1 of FIG. 2 having an oscillatable unit 2 in the form of a fork. Electronic components are arranged on a central section of a circuit board 6. The electronic components serve, for example, for producing the exciter signal and/or for evaluating the received signal with respect to the measured variable. Preferably, the electronic components also include a logic unit, for example, in the form of a microcontroller. Arranged on the circuit board 6 can be, depending on embodiment of the electronics unit of the measuring device 1, some parts of the electronics unit or even the entire electronics unit of the measuring device 1. Arranged in the two end regions of the circuit board 6 are the respective piezoelectric units 41, 42 of FIG. 4a. The piezoelectric units 41, 42 are connected with the electronic components via conductive traces on the circuit board 6. In an alternative embodiment, the piezoelectric units 41, 42 are applied on a sheet or on a plastic board, instead of the circuit board 6.

An advantage of the circuit board 6 is that each of the electrodes of a piezoelectric unit 41, 42 is directly contactable especially simply, for example, by means of a conductive adhesive applicable on a metal area of the circuit board 6.

The end regions of the circuit board 6 are angled, or capable of being bent, relative to the central section in such a manner that the two end regions with the piezoelectric units 41, 42 are introducible into the two hollow spaces 31, 32 in the rod-shaped elements 21, 22, while the central section remains outside the hollow spaces 31, 32. Because of the potting material located in the hollow spaces 31, 32, the two end regions of the circuit board 6 become affixed in the hollow spaces 31, 32. The circuit board 6 is flexibly or rigidly embodied. The integration of the piezoelectric units 41, 42 in a circuit board 6 for forming an electronics module enables an especially fast and secure insertion into the oscillatable unit 2.

FIGS. 4a to 4e illustrate different forms of embodiment of a piezoelectric unit 41. The driving/receiving unit 4 of an oscillatable unit 2 in the form of an oscillatory fork comprises at least two such piezoelectric units 41, 42, which are introduced respectively into hollow spaces 31, 32 of the rod-shaped elements 21, 22. The driving/receiving unit 4 of a single rod comprises, in contrast, preferably only one such piezoelectric unit 41.

Figure 4A:
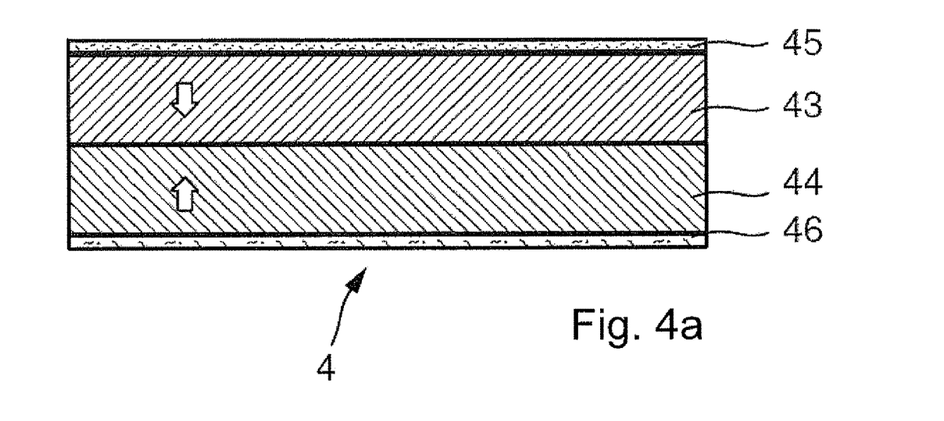
FIG. 4a shows a piezoelectric unit in the form of a piezo bimorph.

FIG. 4a shows a cross section through a piezoelectric unit 41 embodied as a piezo bimorph. The piezoelectric unit 41 is composed essentially of a first piezoelectric element 43 and a second piezoelectric element 44, each of which is of tablet shape and polarized homogeneously. A face of the first piezoelectric element 43 is connected with a face of the second piezoelectric element 44, for example, by means of an adhesive or solder solidly for force coupling. The electrode arising, in such case, as contact surface is, however, not supplied with a potential.

The exposed faces of the piezoelectric elements 43, 44 facing away from one another are coated respectively with electrodes 45, 46, respectively the electrodes 45, 46 are applied on the faces. The electrodes 45, 46 are manufacturable, for example, by means of a structural adhesive, diffusion welding or electrode implementation in the piezoceramic so called cofired electrodes.

The two piezoelectric elements 43, 44 are arranged in such a manner relative to one another that their polarization directions are opposite. The polarization directions are indicated in the figure by arrows. The first electrode 45 and the second electrode 46 are contactable respectively with connection lines for connection with a control/evaluation unit, which controls the supplying of the electrodes 45, 46 with an electrical exciter signal and the receiving of an electrical, received signal from the piezoelectric unit 41 and evaluates such with respect to the process variable.

An alternating voltage is applied to the first electrode 45 and the second electrode 46. A series circuit of the two piezoelectric elements 43, 44 is used. Because of the opposed polarization directions of the piezoelements 43, 44, in such case, the first piezoelectric element 43 shrinks when the second piezoelectric element 44 expands, and vice versa. In total, the piezoelectric unit 41 performs an alternating, bending deformation. The force interlocking connection between the first piezoelectric element 43 and the second piezoelectric element 44 is important, in order that, by means of the joined piezoelectric elements 43, 44, a highest possible bending deformation of the piezoelectric unit 41 arises.

An advantage of a piezoelectric unit 41 embodied according to FIG. 4a is that, because of the equal polarities of the piezoelectric elements 43, 44 at the site of the first electrodes 45 and at the site of the second electrode 46, in each case, even in the case of high temperature jumps, so-called thermal shock, no pyroelectric voltages arise. A measuring device with a driving/receiving unit 4 in the form of one or more of such piezoelectric units 41, 42 is, consequently, especially safe and suitable for use in explosion protected regions.

Figure 4B:
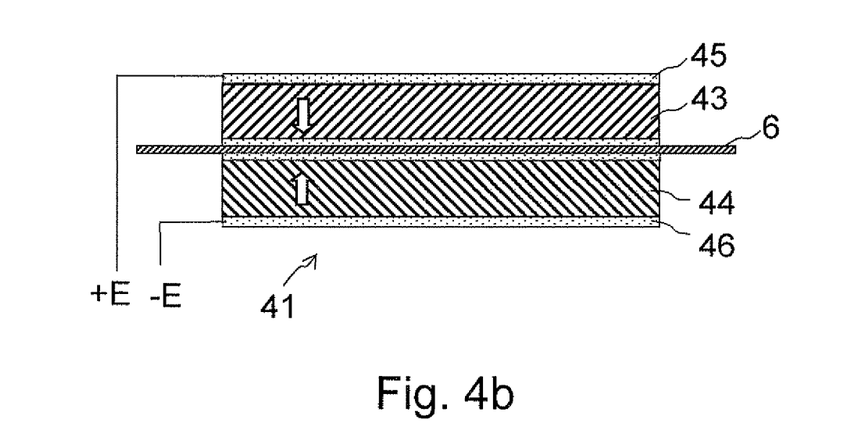
FIG. 4b shows an embodiment of a piezoelectric unit for a module of FIG. 3.

FIG. 4b shows a variant of FIG. 4a, wherein the two piezoelectric elements 43, 44 are likewise polarized in opposite directions. The two piezoelectric elements 43, 44 are, however, not directly adhered to one another, but, instead, at least essentially coincidingly, a thin board 6 is secured to oppositely lying faces. For example, board 6 is a sheet or a circuit board. In a preferred embodiment, the one circuit board is a board, which has no insulation in the region of the piezoelectric elements 43, 44, so that the two faces of the piezoelectric elements 43, 44 facing the board 6 and provided with an electrode, for example, in the form of an electrically conductive coating, are located via the exposed metal layer of the circuit board 6 in conductive contact with one another and have the same electrical potential. The embodiment shown in FIG. 4b is especially suitable for a module of FIG. 3. In the two end regions of the circuit board 6, there are then two piezoelectric elements 43, 44 respectively arranged in such a manner that the circuit board 6 lies between them. Also, in the case of this embodiment, no pyroelectric voltage arises between the two electrodes 45, 46.

Figure 4C:
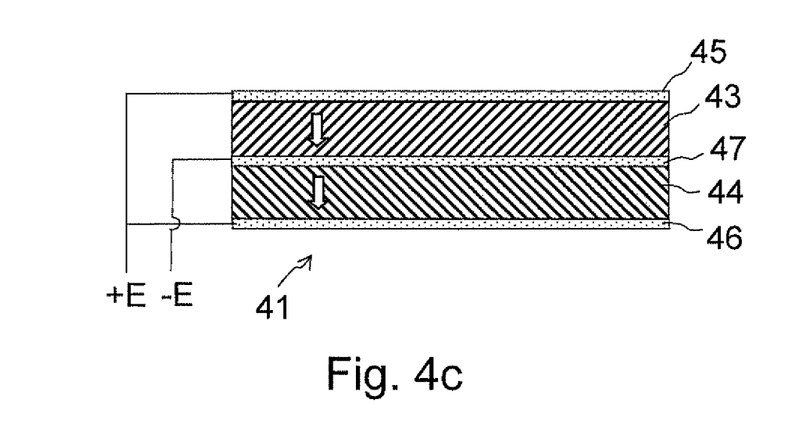
FIG. 4c is a variant of a piezoelectric unit in the form of a piezo bimorph.

FIG. 4c shows an embodiment, in which the polarization direction of the two piezoelectric elements 43, 44 is the same. The contact surface of the two piezoelectric elements 43, 44 is formed by a third electrode 47, which is present, for example, in the form of a metal coating. While the two outer electrodes 45, 46 during the supplying of the exciter signal lie at the same potential, the third electrode 47 located in the middle is at the opposite potential or ground. With this type of voltage supply, there arise the same mechanical stresses in the piezoelectric unit 41 as in the embodiment of FIG. 4a, so that the piezoelectric unit 41 experiences the same bending deformations. However, the deflection is greater than in FIG. 4a, since, because of the effective parallel connection of the two piezoelectric elements 43, 44 instead of the series connection, the complete excitation voltage lies across the first piezoelectric element 43 and across the second piezoelectric element 44. The efficiency of a drive of FIG. 4c is therefore especially high. Additionally, this embodiment is also protected from pyroelectricity.

Figure 4D:
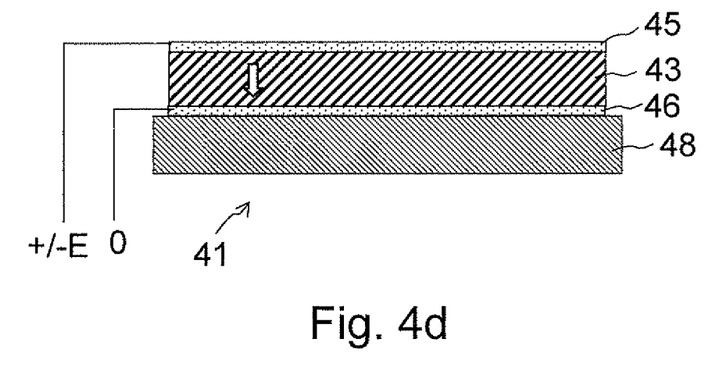
FIG. 4d is a piezoelectric unit having a passive element.

FIG. 4d shows a variant of a piezoelectric unit 41 having only one homogeneously polarized piezoelectric element 43. In order to convert the mechanical stresses, respectively bending forces, arising with the supplying of the exciter signal into a bending deformation, the piezoelectric element 43 is mounted, for example, through adhesive or soldering, with one face against a passive element 48. The passive element 48 is said to be passive, because it possesses no piezoelectric properties and also is not supplied with a voltage. The dimensions of the passive element 48 are preferably at least sufficiently large that the face of the piezoelectric element 43, which forms the contact surface, is completely in contact with the passive element 48. Furthermore, the material of the passive element 48 is selected in such a manner that its modulus of elasticity is similar to that of the piezoelectric material of the piezoelectric element 43 in solid contact with it. For example, the passive element 48 is a disk of a metal, such as e.g. steel, aluminum, titanium, bronze, brass or copper, or of a ceramic, e.g. aluminum oxide, porcelain or soapstone. The exposed face of the piezoelectric element 43 and the contact surface are provided with metal coatings for forming electrodes 45, 46. The electrodes 45, 46 are contactable with the exciter signal.

Figure 4E:
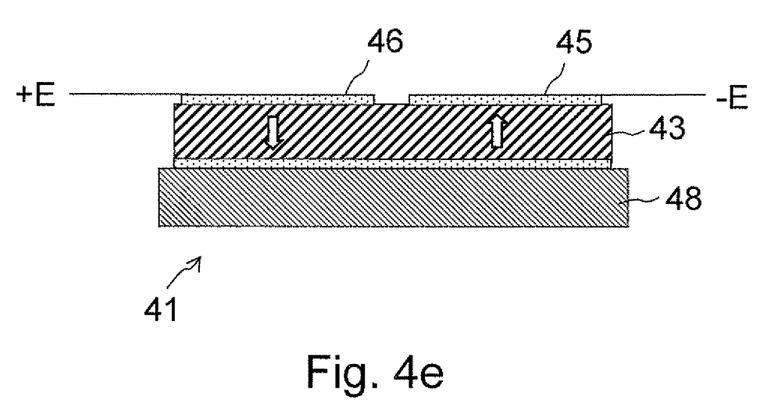
FIG. 4e is a variant of a piezoelectric unit having a passive element.

FIG. 4e shows another variant having a non-piezoelectric, passive element 48. Applied on the tablet-shaped, passive element 48 is a piezoelectric element 43, which has two regions of opposite polarization. The polarization direction extends perpendicular to the contact surface between piezoelectric element. 43 and passive element 48. The two regions on the exposed face of the piezoelectric element 43 are provided respectively with electrodes 45, 46, to which the exciter signal can be applied. The contact surface between piezoelectric element 43 and passive element 48 is embodied as an inactive electrode, i.e. an electrode which does not receive a potential from the driving/receiving unit.

The piezoelectric units 41 illustrated in FIGS. 4a-4e are applicable in measuring devices 1 having an oscillatable unit 2 made of any material. In the case of a metal oscillatable unit 2, the wall of the hollow space 3, 31 is electrically conductive. In order to prevent electrical contact between wall and piezoelectric unit 41, the latter is manufacturable and assemblable in an insulated form of embodiment. The insulation is provided, for example, in the form of a coating, which is applied at least on the two electrodes 45, 46. The coating is, for example, a ceramic or a glass. In an embodiment, the entire piezoelectric unit 41 is encased with an insulating layer. For example, such a coating is manufacturable by potting the piezoelectric unit 41 in an insulating material. Alternatively, the electrodes 45, 46 are covered with respective insulator tablets. For this, especially glass and ceramic tablets are suitable. Likewise suitable as insulating material for the piezoelectric unit 41 is adhesive filled with corundum particles or glass pearls. An advantageous composition comprises 30-60 volume percent epoxide resin and 70-40 volume percent corundum powder or glass pearls.

The piezoelectric units 41 illustrated in FIG. 4a and FIG. 4b are poka-yoke capable. Defective contacting by mixing up the connection wires and defective installed positions in the hollow spaces 3, 31 are not possible. This is very advantageous for manufacturing the measuring devices of the invention. A further advantage for manufacturing in the case of all illustrated embodiments is that the piezoelectric unit 41 need not be oriented in an exact position and secured to another component of the oscillatable unit 2. Instead, the piezoelectric unit 41 can simply be potted, respectively adhered, in the hollow space 3, 31. The piezoelectric unit 41 can be prefabricated and equipped with connection lines, so that only the finished component needs to be assembled. This saves time and effort.

Figure 4F:
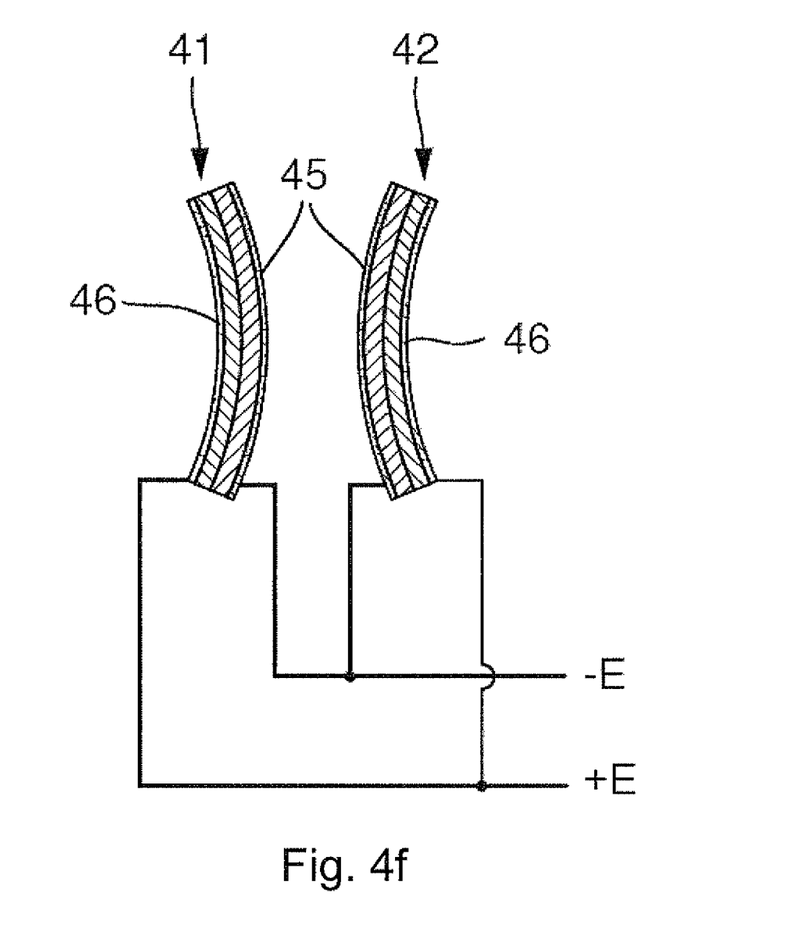
FIG. 4f shows two piezoelectric units for introduction into an oscillatory fork of FIG. 2, with a showing of the electrical contacting.

FIG. 4f shows two piezoelectric units 41, 42 of FIG. 4a under the influence of an alternating voltage. The arrangement of the piezoelectric units 41, 42 corresponds to the assembled state in an oscillatable unit 2 of FIG. 2, i.e. a first piezoelectric unit 41 provided in the first hollow space 31 and a second piezoelectric unit 42 provided in the second hollow space 32.

The mutually facing electrodes 45 of the two piezoelectric units 41, 42 are connected with the same potential −E. The two outer electrodes 46 are connected with the same potential +E. Alternatively, the outer electrodes 46 or the inner electrodes 45 can be connected to ground and the respective other electrodes connected with the potential +/−E. The first piezoelectric unit 41 and the second piezoelectric unit 42 are inwardly curved by the illustrated supplying of voltage, such that the minimum separation of the two piezoelectric units 41, 42 is located between their midpoints. In the case of an opposite supplying, in which case the inner, mutually facing electrodes 45 are connected with the positive potential and the two outer electrodes 46 with the negative potential, the two piezoelectric units 41, 42 are correspondingly curved in the other direction.

If the piezoelectric units 41, 42 are emplaced in the hollow spaces 31, 32 in the root regions of the rod-shaped elements 21, 22 and supplied with an electrical, alternating voltage, the oscillatable unit 2 is excited to execute oscillations in the fundamental mode. In other words, the rod-shaped elements 21, 22 execute oscillations in opposite directions.

A great advantage of this arrangement and embodiment of the driving/receiving unit 4 is the insensitivity to oscillations in unsymmetrical modes, which can arise during use as a result of unwanted vibrations. These are not detected by the piezoelectric units 21, 22, i.e. deflections of the rod-shaped elements 21, 22 in the axial direction, i.e. parallel to the perpendicular to the oscillation direction, as well as asymmetric deflections in the oscillation direction, produce no voltage signal in the piezoelectric elements 43, 44 of the piezoelectric units 41, 42. The measuring device 1 is, consequently, extremely safe from unwanted vibrations. The same holds also for the application of two piezoelectric units 41, 42 according to the other illustrated embodiments.

Figure 5A:
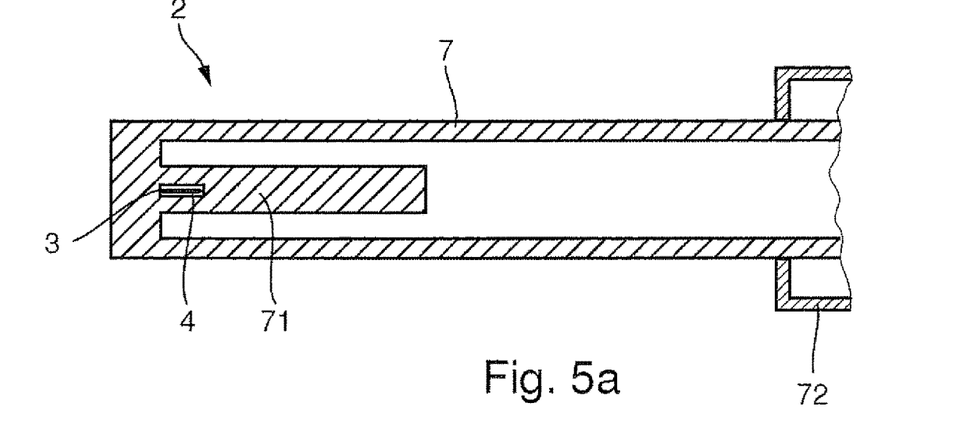
FIG. 5a shows a first embodiment of an oscillatable unit in the form of a single rod having a hollow space.
Figure 5B:
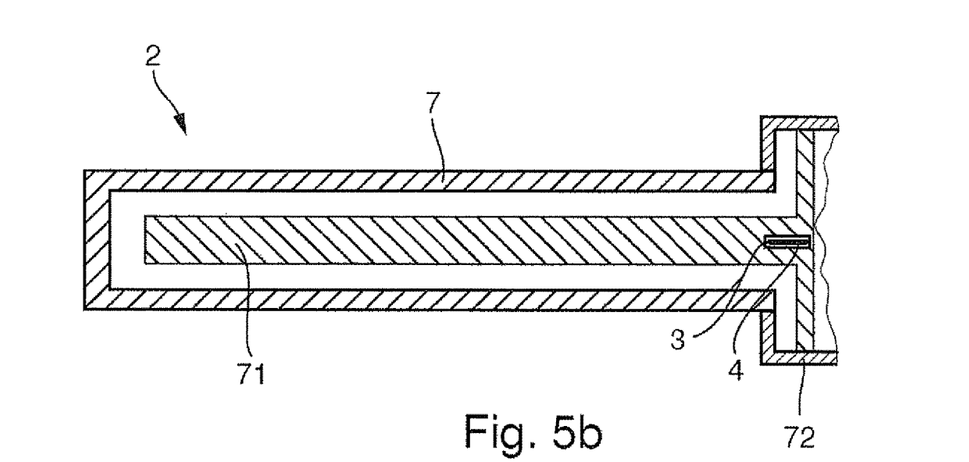
FIG. 5b shows a second embodiment of an oscillatable unit in the form of a single rod having a hollow space.

FIGS. 5a and 5b show, in cross section, two different embodiments of a measuring device having an oscillatable unit 2 in the form of a rod. Such measuring devices, also called single rod devices, are frequently used for fill level measurement of bulk goods and are produced and sold by the applicant under the mark, Soliphant. An advantageously embodied, single rod is described, for example, in WO 2004/094964 A1.

Oscillatable unit 2 is composed of a tubular, hollow body 7 and a rod-shaped inner mass 71. The inner mass 71 can, however, also be formed in another shape than that of a solid rod. An end of the hollow body 7 is connected with a process connection 72, while the other end faces the process. Hollow body 7 and inner mass 71 oscillate in opposite directions. Inner mass 71 and hollow body 7 are dimensioned and matched to one another in such a manner that for each force arising from the oscillations a corresponding counterforce acts, so that essentially no forces act on the clamping, so that the oscillatory system is decoupled.

In the form of embodiment illustrated in FIG. 5a, the inner mass 71 is connected with the hollow body 7 in the process-facing, end region of the hollow body 7. Preferably, the process-facing, end region of the hollow body 7 is sealed with a cap, on which the inner mass 71 is secured, for example, by means of a screwed connection. The driving/receiving unit 4 for exciting the oscillatable unit 2 to bending oscillations and for receiving the mechanical oscillations of the oscillatable unit 2 is placed in a hollow space 3, which is located in the inner mass 71. The hollow space 3 is arranged near to the securement region where the inner mass 71 is secured to the hollow body 7. For example, the hollow space 3 is embodied as a slot and is only slightly larger than the driving/receiving unit 4 located in it. This is especially the case, when the oscillatable unit 2 is composed of a metal. The electrical lines for contacting the driving/receiving unit 4 are guidable through the hollow body 7 and the process connection 72 to an electronics unit (not shown), which preferably is arranged in a housing (likewise not shown). The housing is securable to the process connection 72 on the side facing away from the process.

FIG. 5b shows an alternative form of embodiment of a single rod, wherein the rod-shaped inner mass 71 and the tubular, hollow body 7 are connected with one another in an end region of the hollow body 7 facing away from the process. In such case, the inner mass 71 is secured to a membrane, which is held in the process connection 72. Hollow body 7 is likewise solidly connected with the process connection 72, for example, via a welded or screwed connection. The hollow space 3, in which the driving/receiving unit 4 is located, is situated in the inner mass 71 and near the membrane.

The driving/receiving unit 4 is in both embodiments preferably a piezo bimorph, i.e. a piezoelectric unit 41, such as shown and described with respect to FIG. 4a or FIG. 4c, or a piezo unimorph, such as shown and described with respect to FIG. 4d or FIG. 4e. For the case, in which the inner mass 71 is metal, the driving/receiving unit 4 is preferably coated completely or at least in the region of the electrodes with an insulating material. The potting material provided in the hollow space 3 for affixing the driving/receiving unit 4 and for manufacturing a force interlocked, force coupled, connection with the wall of the hollow space 3, is preferably a hard adhesive. Reference is made here to the paragraphs in the description of FIG. 2 relative to the materials of the oscillatable unit 2 and the potting material. The statements made there concerning oscillatory forks hold analogously for single rods also.

The invention claimed is:

1. An apparatus for determining and/or monitoring at least one process variable of a medium in a container, comprising:
an oscillatable unit for introduction into the container;
a housing, wherein said oscillatable unit is connected with said housing in such a manner that said oscillatable unit closes said housing terminally, and wherein at least one hollow space is introduced in said oscillatable unit which hollow space is accessible from an inner space formed by said housing;
a driving/receiving unit for exciting said oscillatable unit to execute mechanical oscillations and for receiving the mechanical oscillations and for transducing them into an electrical, received signal; and
a control/evaluation unit for controlling the oscillation excitement and for evaluating the received signal with respect to the process variable, wherein:
said driving/receiving unit is introduced into said at least one hollow space and said at least one hollow space is filled with a potting material in such a manner that said driving/receiving unit is tied positively with a wall of said hollow space via the potting material wherein:
for accommodating said driving/receiving unit, a first hollow space is provided in a root region of said first element near to said base and a second hollow space is provided in a root region of said second element near to said base; and
at least two piezoelectric units in the form of a piezo bimorph are applied on a board and said board is embodied in such a manner and said piezoelectric units are arranged on said board in such a manner that said piezoelectric units are introducible into said hollow spaces.

2. The apparatus as claimed in claim 1, wherein:
said piezoelectric unit includes a first tablet-shaped piezoelectric element and a second tablet-shaped piezoelectric element, which are connected for force coupling with one another via respective faces to form a contact surface and which are polarized in the direction perpendicular to said contact surface; and
at least the respective faces of said piezoelectric elements facing away from said contact surface are provided with electrodes for supplying an exciter signal and for tapping a received signal.

3. The apparatus as claimed in claim 1, wherein:
said driving/receiving unit includes at least one piezoelectric unit having a piezoelectric element and a passive element;

said piezoelectric element is contactable with an exciter signal; and said piezoelectric element is connected mechanically with said passive element in such a manner that the supplying of said piezoelectric element with the exciter signal leads to bending deformations of said piezoelectric unit.

4. The apparatus as claimed in claim 1, wherein:
at least said oscillatable unit is composed of a synthetic material or a composite material of synthetic material and glass fibers, glass pearls, carbon fibers and/or ceramic powder.

5. The apparatus as claimed in claim 1, wherein:
at least said oscillatable unit is composed of a metal or a metal alloy, a ceramic, a glass or a composite material of ceramic and glass or ceramic and metal.

6. The apparatus as claimed in claim 1, wherein:
at least for the case, in which said oscillatable unit is composed of an electrically conductive material, at least one covering or coating of an electrically insulating material is applied on said driving/receiving unit.

7. The apparatus as claimed in claim 6, wherein:
said potting material, with which said hollow space is filled and/or the material, with which said driving/receiving unit is coated, is composed essentially of epoxide resin, of epoxide resin and corundum powder, ceramic powder or sand, or of epoxide resin and glass pearls or glass fibers.

8. The apparatus as claimed in claim 1, wherein:
the stiffness of said potting material, with which said hollow space is filled, corresponds essentially to the stiffness of the material of said oscillatable unit.

9. The apparatus as claimed in claim 1, wherein:
said oscillatable unit includes a first rod, or paddle, shaped element and a second rod, or paddle, shaped element, which are connected with one another via a base.

10. The apparatus as claimed in claim 9, wherein:
said control/evaluation unit supplies said driving/receiving unit with an exciter signal in such a manner that said rod, or paddle, shaped elements execute bending oscillations in opposite directions.

11. The apparatus as claimed in claim 1, wherein said oscillatable unit is embodied as a rod-shaped, hollow body with an inner mass formed in an interior of said hollow body on a wall of said hollow body; and
said driving/receiving unit is present in a hollow space provided in said inner mass.

12. The apparatus as claimed in claim 11, wherein:
said inner mass is rod-shaped, and said hollow space with said driving/receiving unit is arranged in such a manner that said inner mass and said hollow body execute bending oscillations in opposite directions.

13. The apparatus as claimed in claim 1, wherein:
said control/evaluation unit comprises part of a module including electronic components for producing the exciter signal and/or for evaluating the received signal with respect to the measured variable.

* * * * *